US011147602B2

(12) United States Patent
Prevost

(10) Patent No.: US 11,147,602 B2
(45) Date of Patent: Oct. 19, 2021

(54) SPINAL IMPLANT SYSTEM AND METHOD

(71) Applicant: Warsaw Orthopedic, Inc, Warsaw, IN (US)

(72) Inventor: Julien J. Prevost, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 71 days.

(21) Appl. No.: 15/586,469

(22) Filed: May 4, 2017

(65) Prior Publication Data

US 2018/0317971 A1 Nov. 8, 2018

(51) Int. Cl.
*A61B 17/86* (2006.01)
*A61B 17/70* (2006.01)

(52) U.S. Cl.
CPC ...... *A61B 17/8605* (2013.01); *A61B 17/7037* (2013.01); *A61B 17/7098* (2013.01); *A61B 17/864* (2013.01); *A61B 17/8635* (2013.01); *A61B 17/7032* (2013.01); *A61B 17/861* (2013.01); *A61B 17/8615* (2013.01)

(58) Field of Classification Search
CPC ............ A61B 17/7032; A61B 17/7035; A61B 17/8605; A61B 17/7037; A61B 17/7038; A61B 17/861; A61B 17/863; A61B 17/864; A61B 17/8615; A61B 17/7098
USPC .................. 606/305, 304, 269, 270
See application file for complete search history.

(56) References Cited

U.S. PATENT DOCUMENTS

| | | | |
|---|---|---|---|
| 6,214,012 B1* | 4/2001 | Karpman | A61B 17/864 606/246 |
| 6,485,491 B1* | 11/2002 | Farris | A61B 17/7002 606/250 |
| 7,785,356 B2* | 8/2010 | Biedermann | A61B 17/7032 606/266 |
| 8,574,273 B2 | 11/2013 | Russell et al. | |
| 8,945,193 B2 | 2/2015 | Kirschman | |
| 8,992,587 B2 | 3/2015 | Kirschman | |
| 9,078,701 B2 | 7/2015 | Thalgott et al. | |
| 9,119,674 B2* | 9/2015 | Matthis | A61B 17/7032 |
| 9,173,692 B1* | 11/2015 | Kaloostian | A61B 17/8615 |
| 9,265,540 B2 | 2/2016 | Kirschman | |
| 9,326,801 B2* | 5/2016 | Poulos | A61B 17/7098 |
| 9,333,018 B2 | 5/2016 | Russell et al. | |
| 9,592,081 B2 | 3/2017 | Thalgott et al. | |
| 10,568,667 B2* | 2/2020 | Biester | A61B 17/7001 |
| 2008/0132957 A1* | 6/2008 | Matthis | A61B 17/8685 606/301 |
| 2009/0204155 A1* | 8/2009 | Aschmann | A61B 17/7032 606/264 |
| 2010/0030135 A1* | 2/2010 | Mitchell | A61M 31/00 604/48 |

(Continued)

FOREIGN PATENT DOCUMENTS

WO 2014149746 A1 9/2014

*Primary Examiner* — Marcela I. Shirsat
(74) *Attorney, Agent, or Firm* — Sorell, Lenna & Schmidt, LLP

(57) ABSTRACT

A bone fastener includes a distal member having a proximal portion and a closed distal tip. The distal member includes an outer surface engageable with a first cortical surface and a second cortical surface. The proximal portion includes an inner surface that defines a longitudinal cavity and at least one fenestration in communication therewith. Systems, spinal constructs, surgical instruments and methods are disclosed.

22 Claims, 4 Drawing Sheets

(56) References Cited

U.S. PATENT DOCUMENTS

| | | | |
|---|---|---|---|
| 2011/0190825 A1 | 8/2011 | Thalgott et al. | |
| 2011/0288599 A1* | 11/2011 | Michielli | A61B 17/7037 606/305 |
| 2012/0022603 A1 | 1/2012 | Kirschman | |
| 2013/0053901 A1* | 2/2013 | Cormier | A61B 17/7037 606/305 |
| 2014/0058461 A1 | 2/2014 | Black | |
| 2014/0121703 A1* | 5/2014 | Jackson | A61B 17/7032 606/246 |
| 2015/0157366 A1 | 6/2015 | Kirschman | |
| 2015/0196371 A1 | 7/2015 | Westover | |
| 2016/0008039 A1 | 1/2016 | Thalgott et al. | |

* cited by examiner

SPINAL IMPLANT SYSTEM AND METHOD

TECHNICAL FIELD

The present disclosure generally relates to medical devices for the treatment of spinal disorders, and more particularly to a surgical implant system including a bone fastener and a related method.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a bone fastener is provided. The bone fastener includes a distal member having a proximal portion and a closed distal tip. The distal member includes an outer surface engageable with a first cortical surface and a second cortical surface. The proximal portion includes an inner surface that defines a longitudinal cavity and at least one fenestration in communication therewith. In some embodiments, systems, spinal constructs, surgical instruments and methods are disclosed.

BRIEF DESCRIPTION OF THE DRAWINGS

The present disclosure will become more readily apparent from the specific description accompanied by the following drawings, in which.

DETAILED DESCRIPTION

Figures 1, 2:
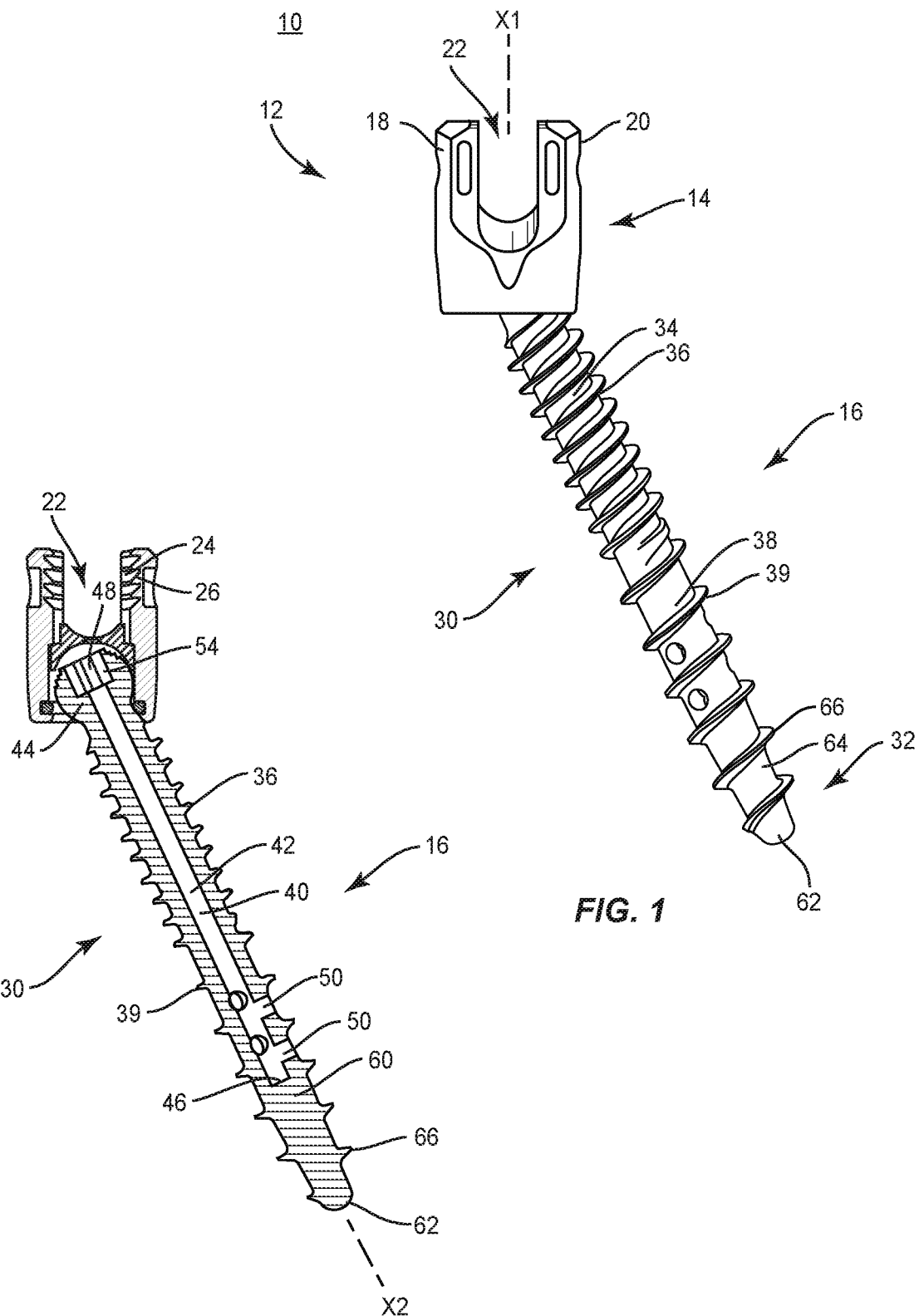
FIG. 1 is a side view of components of one embodiment of a system in accordance with the principles of the present disclosure.
FIG. 2 is a cross section view of the components shown in FIG. 1.

The exemplary embodiments of a surgical system and related methods of use disclosed are discussed in terms of medical devices for the treatment of musculoskeletal disorders and more particularly, in terms of a spinal implant system including a fenestrated bone screw and a method for treating one or more spinal disorders.

In some embodiments, the surgical system of the present disclosure comprises a spinal implant, such as, for example, a bone screw that is engageable with cortical tissue surfaces of one or more vertebral levels. In some embodiments, the surgical system of the present disclosure comprises a bi-cortical fenestrated bone screw. In some embodiments, the bone screw includes a proximal member, such as, for example, an implant receiver and a distal member, such as, for example, a bi-cortical shaft. In some embodiments, the bone screw can include various configurations, such as, for example, a posted screw, a pedicle screw, a bolt, a bone screw for a lateral plate, a uni-axial screw (UAS), a fixed angle screw (FAS), a multi-axial screw (MAS), a side loading screw, a sagittal adjusting screw (SAS), a transverse sagittal adjusting screw (TSAS), an awl tip (ATS) or a sacral bone screw.

In some embodiments, the surgical system of the present disclosure comprises a bone screw including a fenestrated shaft that maintains bi-cortical purchase. In some embodiments, the bone screw includes fenestrations that are disposed proximally from a distal tip of the shaft to facilitate cortical purchase of the distal tip. In some embodiments, the bone screw includes a cannulated portion configured to extend a distance along the shaft such that the distal tip is solid. In some embodiments, the positioning of the cannulated portion along a distance of the shaft is configured to prevent leakage of cement outside a vertebral body. In some embodiments, the distal tip includes various configurations to facilitate engagement with tissue. In some embodiments, the surgical system of the present disclosure includes a bone screw that provides bi-cortical fixation to enhance fixation with vertebrae and reduce the risk of screw loosening when used with a biologic or agent, for example, bone cement (PMMA), and/or reduce the risk of biologic or agent leakage outside of a vertebral body.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1 and 2 there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal implant, such as, for example, a bone fastener 12. Bone fastener 12 comprises a proximal member, such as, for example, an implant receiver 14 and a distal member, such as, for example, an elongated shaft 16. In some embodiments, bone fastener 12 is configured to facilitate bi-cortical fixation and enhance purchase with cortical bone of a vertebra, as described herein. In some embodiments, bone fastener 12 provides bi-cortical fixation to enhance fixation with vertebrae and reduce the risk of screw loosening when used with a biologic or agent, for example, bone cement (PMMA), and/or reduce the risk of biologic or agent leakage outside of a vertebral body.

Receiver 14 extends along and defines an axis X1. Receiver 14 includes a pair of spaced apart arms 18, 20 that define an implant cavity 22 therebetween configured for disposal of a component of a spinal construct, such as, for example, a spinal rod (not shown). Arms 18, 20 extend parallel to axis X1. In some embodiments, arm 18 and/or arm 20 may be disposed at alternate orientations, relative to axis X1, such as, for example, transverse, perpendicular and/or other angular orientations such as acute or obtuse, coaxial and/or may be offset or staggered. Arms 18, 20 each include an arcuate outer surface extending between a pair of side surfaces. At least one of the outer surfaces and the side surfaces of arms 18, 20 have at least one recess or cavity therein configured to receive an insertion tool, compression instrument and/or instruments for inserting and tensioning bone fastener 12. In some embodiments, arms 18, 20 are connected at proximal and distal ends thereof such that receiver 14 defines a closed spinal rod slot.

Cavity 22 is substantially U-shaped. In some embodiments, all or only a portion of cavity 22 may have alternate cross section configurations, such as, for example, closed, V-shaped, W-shaped, oval, oblong triangular, square, polygonal, irregular, uniform, non-uniform, offset, staggered, and/or tapered. Receiver 14 includes an inner surface 24. A portion of surface 24 includes a thread form 26. Thread form 26 is configured for engagement with a coupling member, such as, for example, a setscrew (not shown), to retain the spinal rod within cavity 22. In some embodiments, surface 24 may be disposed with the coupling member in alternate fixation configurations, such as, for example, friction fit, pressure fit, locking protrusion/recess, locking keyway and/or adhesive. In some embodiments, all or only a portion of surface 24 may have alternate surface configurations to enhance engagement with the spinal rod and/or the setscrew, such as, for example, rough, arcuate, undulating, mesh, porous, semi-porous, dimpled and/or textured. In some embodiments, receiver 14 may include alternate configurations, such as, for example, closed, open and/or side access.

In some embodiments, receiver 14 is connectable with shaft 16 to form a multi-axial screw (MAS). In some embodiments, connection of receiver 14 with shaft 16 can be actuated by a manual engagement and/or non-instrumented assembly, which may include a practitioner, surgeon and/or medical staff grasping receiver 14 and shaft 16 and forcibly snap or pop fitting the components together. In some embodiments, receiver 14 is connectable with shaft 16 to include various configurations, such as, for example, a uni-axial screw (UAS), a fixed angle screw (FAS), a side loading screw, a sagittal adjusting screw (SAS), a transverse sagittal adjusting screw (TSAS), an awl tip screw (ATS) or a sacral bone screw.

Figure 3:
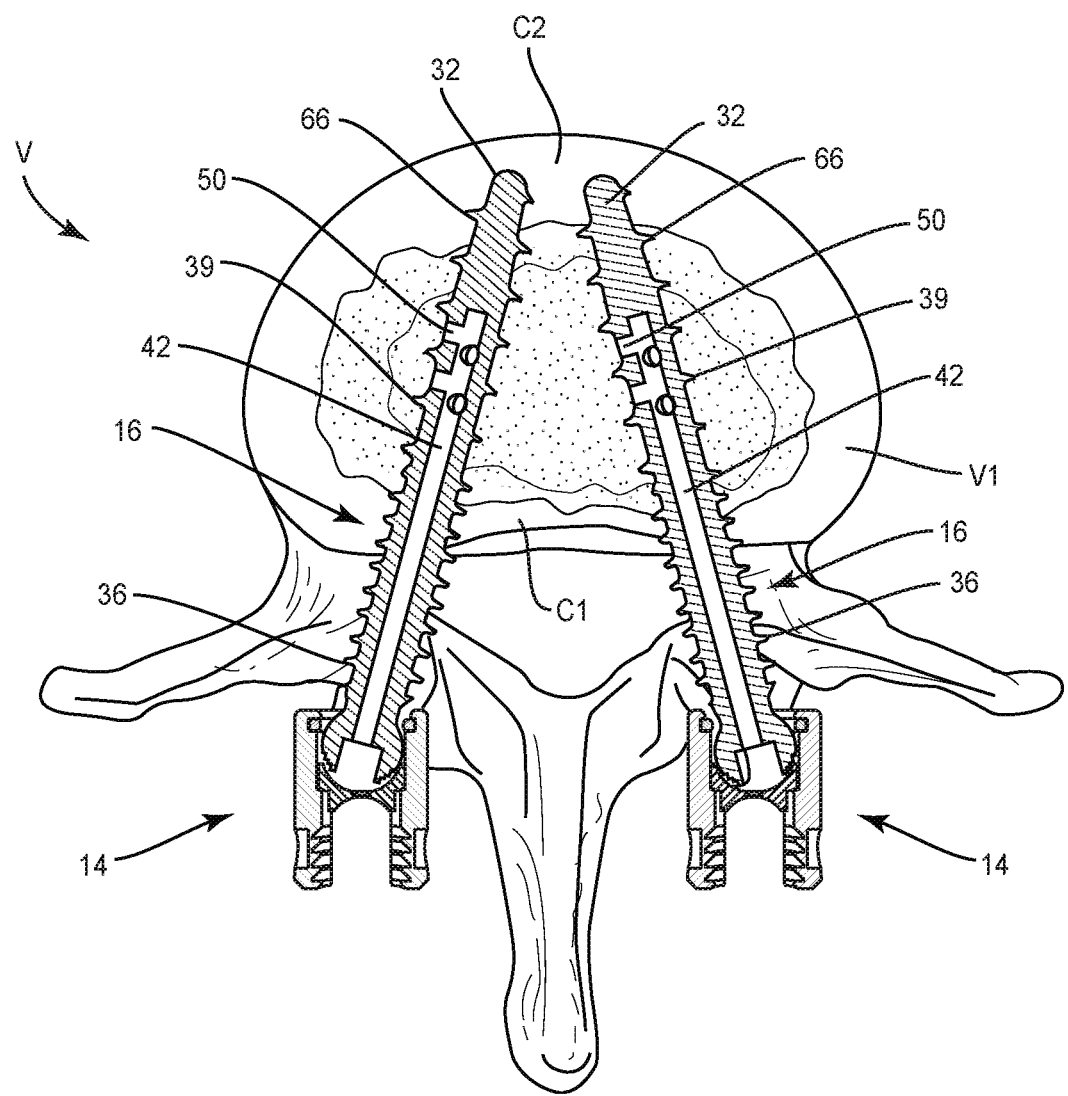
FIG. 3 is an axial view of components of one embodiment of a system in accordance with the principles of the present disclosure disposed with vertebrae.

Shaft 16 extends along an axis X2 between a proximal portion 30 and a closed distal tip 32. Shaft 16 is configured for bi-cortical fixation with vertebrae, as described herein. Portion 30 includes a proximal surface 34 having a thread 36. Thread 36 is oriented with shaft 16 and disposed for engagement with a cortical surface, such as, for example, a cortical layer portion C1 of a vertebral level of vertebrae V, as shown in FIG. 3. Portion 30 includes a distal surface 38 having a thread 39. Thread 39 is oriented with shaft 16 and disposed for engagement with cancellous tissue of a vertebral level of vertebrae V. Threads 36, 39 are disposed in a serial orientation along shaft 16.

In some embodiments, thread 36 includes a fine, closely-spaced and/or shallow configuration to facilitate and/or enhance engagement with cortical layer portion C1. In some embodiments, thread 36 includes a smaller pitch or more thread turns per axial distance of shaft 16 relative to thread 39 such that thread 36 provides a stronger fixation with vertebral tissue and/or resists loosening from tissue. In some embodiments, thread 39 includes a greater pitch and an increased lead between thread turns relative to thread 36. In some embodiments, thread 36 is continuous along shaft 16. In some embodiments, thread 39 is continuous along shaft 16.

In some embodiments, threads 36, 39 may be intermittent, staggered, discontinuous and/or may include a single thread turn or a plurality of discrete threads. In some embodiments, other penetrating elements may be located on shaft 16, such as, for example, a nail configuration, barbs, expanding elements, raised elements, ribs, and/or spikes to facilitate engagement of shaft 16 with tissue. In some embodiments, threads 36, 39 may be self-tapping or intermittent.

Portion 30 includes an inner surface 40 that defines a longitudinal cavity, such as, for example, passageway 42 such that bone fastener 12 includes a cannulated configuration. Passageway 42 extends along axis X2. Passageway 42 is configured to direct and/or guide an agent disposed therein into a vertebral body to enhance fixation, facilitate bone growth, provide therapy and/or diagnosis, as described herein. In some embodiments, passageway 42 is configured to direct and/or guide bone cement into a vertebral body to facilitate fixation of bone fastener 12 with tissue, as described herein. Surface 40 extends between a proximal end 44 and a distal most end 46. Passageway 42 extends through portion 30, and is discontinuous and includes a closed configuration adjacent a proximal end of tip 32, as described herein. End 46 is disposed in a spaced apart relation relative to a distal end of tip 32. This configuration of end 46 and tip 32 resist and/or prevent the release of an agent external and/or outside of a vertebral body. As such, the agent can be confined within the vertebral body to resist and/or prevent leakage to non-select body regions. In some embodiments, passageway 42 extends longitudinally through all of shaft 16 such that bone fastener 12 is cannulated along the entire length of shaft 16 including tip 32.

End 44 defines an axial opening 48 disposed in communication with passageway 42. In some embodiments, opening 48 is in communication with cavity 22 of receiver 14. In some embodiments, passageway 42 may be disposed in various orientations, such as, for example, perpendicular, transverse and/or at angular orientations, such as acute or obtuse relative to axis X2.

Portion 30 includes a plurality of lateral openings, such as, for example, fenestrations 50. Fenestrations 50 define a lateral passageway that extends from passageway 42 through a wall thickness of portion 30 between surfaces 34, 40. Fenestrations 50 are in communication with passageway 42 to facilitate a flow of an agent from passageway 42 into a vertebral body, as described herein. In some embodiments, fenestrations 50 are disposed perpendicular relative to passageway 42. In some embodiments, fenestrations 50 may be disposed at alternate orientations, relative to passageway 42, such as, for example, transverse and/or other angular orientations such as acute or obtuse, coaxial and/or may be offset or staggered. In some embodiments, fenestrations 50 include a tapered configuration. Fenestrations 50 are disposed in a serial orientation along passageway 42, as shown in FIG. 2. In some embodiments, fenestrations 50 allow the flow of an agent disposed within passageway 42 external to shaft 16.

In some embodiments, the agent may include bone growth promoting material, such as, for example, bone graft to enhance fixation of bone fastener 12 and/or other components of a spinal construct with tissue, as described herein. Osteogenic material may be included in the agent such as, for example, autologous bone harvested from the patient receiving the implant device, bone allograft, bone xenograft, any number of non-bone implants (for example ceramic, metallic, polymer), bone morphogenic protein, and/or bioresorbable compositions. In some embodiments, the agent can contain other bioactive agents or other active agents, which may include one or a plurality of therapeutic agents and/or pharmacological agents for release, including sustained release, into a vertebra to treat, for example, pain, inflammation and degeneration. The agents may include pharmacological agents, such as, for example, antibiotics, pain medications, analgesics, anesthetics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof. In some embodiments, the agent may include bone cement that enhances fixation of bone fastener 12 with tissue. In some embodiments, the bone cement may include a poly(methyl methacrylate) (PMMA); methyl methacrylate (MMA); calcium phosphate; a resorbable polymer, such as, for example, PLA, PGA or combinations thereof; a resorbable polymer with allograft, such as, for example, particles or fibers of mineralized bone and/or combinations thereof.

End 44 includes a socket 54 configured for engagement with a drive surface of a surgical driver instrument, as described herein. Socket 54 defines a hexalobular cross section for disposal and engagement of a correspondingly shaped portion of the drive surface. In some embodiments, socket 54 defines a cruciform, phillips, square, polygonal or star cross sectional configuration for disposal and engagement of a correspondingly shaped portion of the drive surface. The surface of end 44 defining socket 54 comprises a portion of a torque interface between a surgical instrument to drive, rotate, torque, insert, implant or otherwise connect bone fastener implant 12 with tissue, as described herein.

Tip 32 extends between a proximal end 60 and distal end 62. Tip 32 includes a surface 64 having a thread 66. Thread 66 is oriented with tip 32 and disposed for engagement with a cortical surface, such as, for example, a cortical layer portion C2 of a vertebral level of vertebrae V, as shown in FIG. 3. Thread 66 is continuous with thread 39 along tip 32 and includes a similar configuration. In some embodiments, thread 66 may be alternatively configured, similar to threads 36, 39, described herein.

End 60 is disposed adjacent end 46 of passageway 42 and spaced apart from end 62. Tip 32 includes a solid, non-cannulated configuration. As such, an agent, as described herein, transferred through passageway 42 and expelled through fenestrations 50 is maintained within a vertebral body upon fixation of bone fastener 12 with the vertebral body. Fenestrations 50 allow the flow of an agent disposed within passageway 42 external to shaft 16 and within the vertebral body while tip 32 resists and/or prevents expulsion of an agent external and/or outside of a vertebral body. As such, the agent can be confined within the vertebral body to resist and/or prevent leakage. In some embodiments, a portion of tip 32 may extend external or protrude from an outer surface of a cortical layer of a vertebral body upon fixation of bone fastener 12 with tissue.

In some embodiments, tip 32 includes a hollow configuration that defines a cavity in tip 32 that is spaced apart and/or sealed from passageway 42, and/or sealed from tissue or bodily fluids. In some embodiments, tip 32 is tapered, for example, with a bevel for easier insertion and less tearing of the tissue. In some embodiments, tip 32 includes a tapered configuration. In some embodiments, surface 64 is oriented at an angle in a range of 0 through 15 degrees relative to axis X2. In some embodiments, end 62 of tip 32 has a blunt configuration. In some embodiments, end 62 of tip 32 includes a sharpened point.

In assembly, operation and use, spinal implant system 10, similar to the systems and methods described herein, includes bone fastener 12 and is employed with a surgical procedure for treatment of a spinal disorder affecting a section of a spine of a patient, as discussed herein. The components of spinal implant system 10 are employed with a surgical procedure for treatment of a condition or injury of an affected section of the spine, such as, for example, vertebrae V, as shown in FIG. 3.

In use, to treat a selected section of vertebrae V, a medical practitioner obtains access to a surgical site including vertebrae V. In some embodiments, spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of vertebrae V, as well as for aspiration and irrigation of a surgical region.

Pilot holes are made in a vertebral level V1 of vertebrae V in a selected orientation for disposal of one or more bone fasteners 12. Bone fasteners 12 are engaged with a surgical driver instrument, as described herein, for orientation and disposal with the pilot holes. Each bone fastener 12 is aligned with the pilot hole and the driver is torqued or otherwise rotated such that shaft 16 translates axially within the pilot hole for engagement with the tissue of vertebral level V1.

Threads 66, 39, 36, as described herein, engage and pass through cortical layer portion C1 of vertebral level V1 such that shaft 16 axially translates through the tissue of vertebral level V1. Tip 32 translates through cortical layer portion C1 and the cancellous tissue of vertebral level V1 into engagement with cortical layer portion C2. Thread 66 engages cortical layer portion C2 for fixation with cortical layer portion C2. Threads 39 engage and are fixed with the cancellous tissue of vertebral level V1. Translation of shaft 16 with the tissue of vertebral level V1 orients and disposes thread 36 for engagement and fixation with cortical layer portion C1. As such, bone fastener 12 is implanted with vertebral level V1 and shaft 16 is fixed with the tissue of vertebral level V1 in a bi-cortical engagement and fixation. In some embodiments, threads 66 engage and are fixed with the cancellous tissue of vertebral level V1 and/or extend external or protrude from cortical layer portion C2.

Bone fastener 12 is fixed with vertebral level V1 and portion 30 is disposed with the cancellous tissue of vertebral level V1. Distal surface 38 is disposed with the cancellous tissue such that fenestrations 50 are oriented with the cancellous tissue and within the cortical layer of vertebral level V1. An injection device, such as, for example, a syringe or a pump including a port for connection with opening 48 is connected with a source of an agent, as described herein. The agent is provided to bone fastener 12 via the injection device for transfer to passageway 42. The agent is directed and/or guided into the cancellous tissue of vertebral level V1. The agent flows through passageway 42 and is expelled through fenestrations 50 out of shaft 16 to the cancellous tissue and within the cortical layer of vertebral level V1. Tip 32 is fixed with cortical layer portion C2 and spaced apart from passageway 42 to resist and/or prevent expulsion of the agent external and/or outside of the cortical layer of vertebral level V1. As the agent is expelled from fenestrations 50, the agent is confined within the cortical layer of vertebral level V1 to resist and/or prevent the agent from leaking outside of vertebral level V1.

Upon completion of a procedure, as described herein, the surgical instruments, assemblies and non-implanted components of spinal implant system 10 are removed and the incision(s) are closed. One or more of the components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of rods, plates, connectors and/or bone fasteners for use with a single vertebral level or a plurality of vertebral levels.

In some embodiments, spinal implant system 10 comprises a kit including a plurality of bone fasteners 12 of varying configuration, as described herein. In some embodiments, bone fastener 12 is selected from the kit for employing with a treatment at the surgical site. In some embodiments, bone fastener 12 is connected with a surgical instrument to facilitate insertion and manipulation of bone fastener 12 utilizing an image guide, such as, for example, a navigation component (not shown) of a medical imaging and navigation system (not shown), as described herein. The navigation component is configured to generate a signal representative of a position of the surgical instrument and bone fastener 12 to the navigation system. In some embodiments, the image guide may include one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals.

Figure 4:
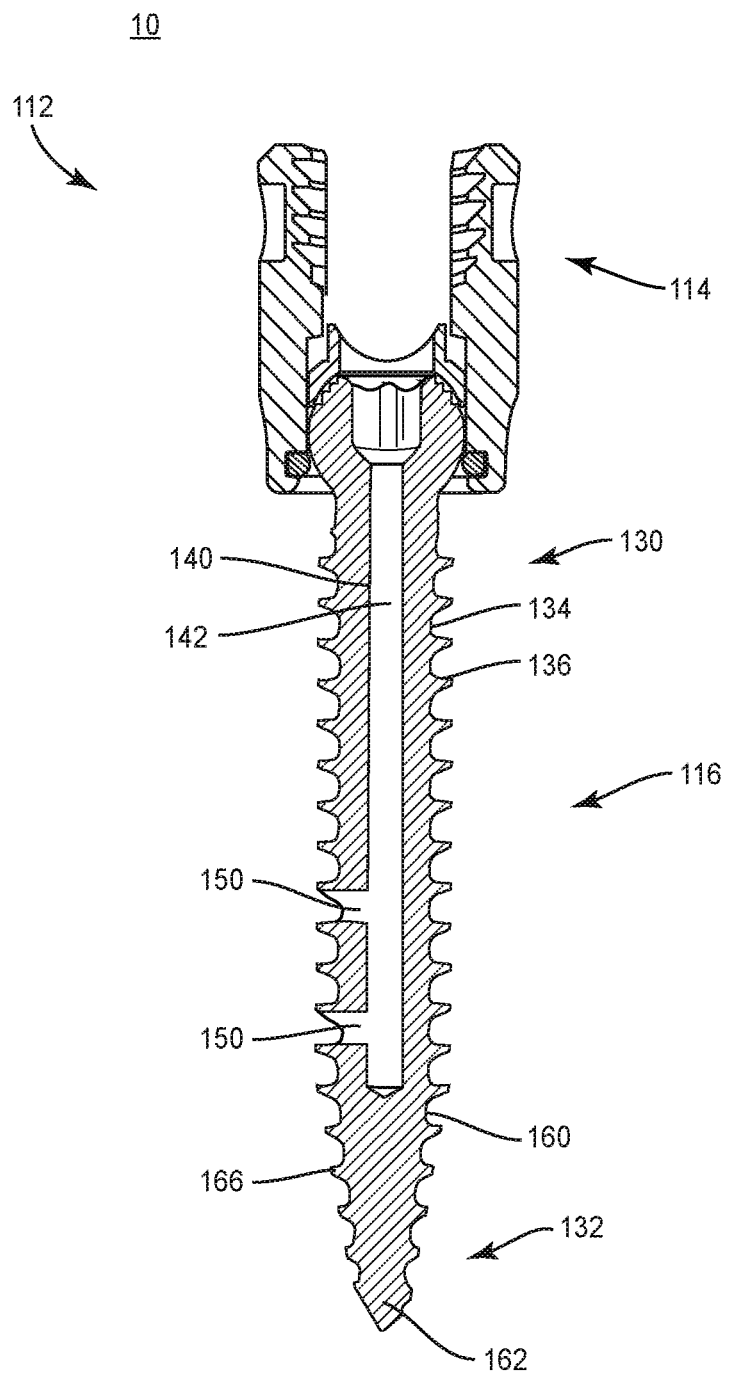
FIG. 4 is a cross section view of components of one embodiment of a system in accordance with the principles of the present disclosure.

In one embodiment, as shown in FIG. 4, spinal implant system 10, similar to the systems and methods described herein, includes a bone faster 112, similar to bone fastener 12 described herein. Bone fastener 112 comprises an implant receiver 114, similar to receiver 14 described herein, and an elongated shaft 116, similar to shaft 16 described herein. Bone fastener 112 is configured to facilitate bi-cortical fixation with vertebrae, as described herein. Receiver 114 is connectable with shaft 116 to form a multi-axial screw (MAS). Shaft 116 extends between a proximal portion 130 and a closed distal tip 132, similar to tip 32 described herein. Shaft 116 includes a surface 134 that includes a thread 136, similar to the threads described herein, configured for engagement with tissue of vertebrae, as described herein. Portion 130 includes a surface 140 that defines a passageway 142, similar to passageway 42 described herein. Portion 130 includes a plurality of fenestrations 150, similar to fenestrations 50 described herein. Tip 132 extends between a proximal end 160 and distal end 162, and includes a thread 166 configured for engagement with tissue of vertebrae, as described herein. Tip 132 is tapered to define an awl tip to facilitate self-tapping for engagement with vertebrae.

Figure 5:
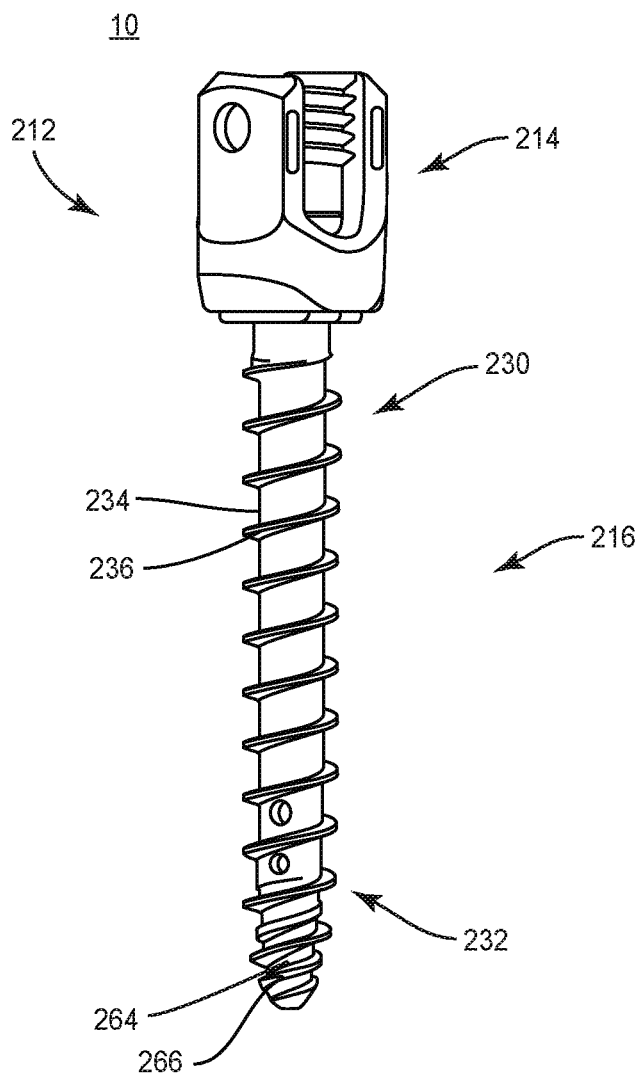
FIG. 5 is a side view of components of one embodiment of a system in accordance with the principles of the present disclosure.
Figure 6:
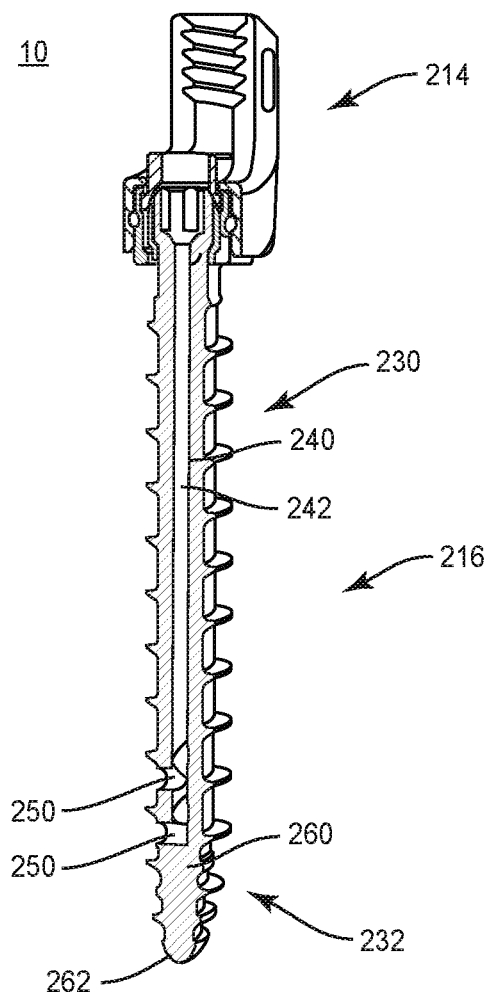
FIG. 6 is a cross section view, in part cutaway, of the components shown in FIG. 5.

In one embodiment, as shown in FIGS. 5 and 6, spinal implant system 10, similar to the systems and methods described herein, includes a bone faster 212, similar to bone fastener 12 described herein. Bone fastener 212 comprises an implant receiver 214, similar to receiver 14 described herein, and an elongated shaft 216, similar to shaft 16 described herein. Bone fastener 212 is configured to facilitate bi-cortical fixation with vertebrae, as described herein. Receiver 214 is connectable with shaft 216 to form a sacral iliac screw to connect bone fastener 212 with the cortical surface portions of a sacroiliac joint and adjacent bone of the ilium and sacrum.

Shaft 216 extends between a proximal portion 230 and a closed distal tip 232, similar to tip 32 described herein. Shaft 216 includes a surface 234 that includes a thread 236, similar to the threads described herein, and configured for engagement with sacral and/or iliac bone. Portion 230 includes a surface 240 that defines a passageway 242, similar to passageway 42 described herein. Portion 230 includes a plurality of fenestrations 250, similar to fenestrations 50 described herein. Tip 232 extends between a proximal end 260 and distal end 262, and includes a surface 264 that includes a thread 266 configured for engagement with a sacrum bone, similar to that described herein. In some embodiments, tip 232 is tapered, for example, with a bevel for easier insertion and less tearing of the tissue, such as the cortical layers of the ilium and the sacrum.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fastener comprising:
 a monolithic proximal member defining an implant cavity and a groove;
 a monolithic distal member extending along a longitudinal axis between a proximal portion and a closed distal tip, the distal member further including a first thread configured to engage with a first cortical layer of a patient in use of the bone fastener and a second thread distinct from the first thread and configured to engage with a second cortical layer of the patient in use of the bone fastener, the proximal portion defining only one longitudinal cavity and a socket in communication with the longitudinal cavity, the socket including a first portion having a polygonal configuration and a second portion, the second portion being continuously tapered from the first portion to the longitudinal cavity, the proximal portion comprising a first column of fenestrations and a second column of fenestrations, the first column of fenestrations being offset from the second column of fenestrations about the longitudinal axis, the fenestrations each being in communication with the longitudinal cavity, the distal member being made entirely from one or more of the group consisting of metals, synthetic polymers and ceramics; and
 band surrounds at least a portion of the distal member to couple the distal member to the proximal member.

2. A bone fastener as recited in claim 1, wherein the proximal portion includes the first thread and the distal tip includes the second thread.

3. A bone fastener as recited in claim 1, wherein the distal tip extends between a proximal end and a distal end, the proximal end being disposed adjacent the longitudinal cavity.

4. A bone fastener as recited in claim 1, wherein the distal tip extends between a proximal end and a distal end, the longitudinal cavity including a distal most end, the distal most end being spaced apart from the distal end of the distal tip.

5. A bone fastener as recited in claim 1, wherein the distal tip is solid.

6. A bone fastener as recited in claim 1, wherein the distal tip includes a tapered configuration.

7. A bone fastener as recited in claim 1, wherein the distal tip includes an outer surface oriented at an angle in a range of 0 through 15 angular degrees relative to the longitudinal axis.

8. A bone fastener as recited in claim 1, wherein the distal tip includes a blunt configuration.

9. A bone fastener as recited in claim 1, wherein the proximal portion is cannulated.

10. A bone fastener as recited in claim 1, wherein the first portion defines an axial opening in communication with the longitudinal cavity.

11. A bone fastener as recited in claim 1, wherein the first column of fenestrations includes a distalmost fenestration, the distalmost fenestration defining a distalmost end of the longitudinal cavity.

12. A bone fastener as recited in claim 1, wherein the first column of fenestrations includes a first fenestration and a second fenestration, the second column of fenestrations including a third fenestration and a fourth fenestration, the third fenestration being positioned along the longitudinal axis between the first fenestration and the second fenestration.

13. A bone fastener as recited in claim 1, wherein the first and second columns each extend parallel to the longitudinal axis, the second column being spaced radially about the longitudinal axis less than 180 degrees from the first column.

14. A bone fastener as recited in claim 1, wherein the first and second columns each extend parallel to the longitudinal axis, the second column being spaced radially about the longitudinal axis 90 degrees from the first column.

15. A bone fastener comprising:
a monolithic implant receiver defining a chamber and a groove in communication with the chamber;
a monolithic bi-cortical shaft extending along a longitudinal axis between a proximal portion and a closed distal tip, the shaft defining only one longitudinal passageway and a socket in communication with the longitudinal passageway, the socket including a first portion having a first maximum diameter and a second portion having a reduced second maximum diameter, the second portion being continuously tapered from the first portion to the longitudinal cavity, the proximal portion comprising a first column of lateral openings and a second column of lateral openings, the first column of lateral openings being offset from the second column of lateral openings about the longitudinal axis, the lateral openings each being disposed in communication with the passageway, the shaft comprising a first thread configured to engage with a first cortical surface and a second thread configured to engage a second cortical surface, the fenestrations being spaced apart from the threads, the shaft being made entirely from one or more of the group consisting of metals, synthetic polymers and ceramics;
a crown positioned in the chamber such that the crown engages a head of the shaft; and
a band positioned in the groove such that the band surrounds at least a portion of the shaft to couple the shaft to the receiver.

16. A bone fastener as recited in claim 15, wherein the implant receiver is rotatable relative to the shaft in a multi-axial configuration.

17. A bone fastener as recited in claim 15, wherein the implant receiver is rotatable relative to the shaft in a sagittal adjustable configuration.

18. A bone fastener as recited in claim 15, wherein the first portion defines an axial opening disposed in communication with the longitudinal passageway, the axial opening having a hexalobular cross section.

19. A bone fastener as recited in claim 15, wherein the longitudinal passageway communicates with the lateral openings.

20. A bone fastener as recited in claim 15, wherein the lateral openings each extend through a wall thickness of the shaft and extend in a perpendicular orientation relative to the longitudinal passageway.

21. A bone fastener comprising:
a monolithic receiver including an inner surface defining a chamber and a groove in communication with the chamber, the receiver including spaced apart arms, the arms defining a portion of a U-shaped implant cavity, the arms each including a threaded inner surface configured for engagement with a set screw;
a monolithic elongated shaft connected with the receiver such that the receiver is rotatable relative to the shaft, the shaft extending along a longitudinal axis between a proximal portion and a blunt distal tip, the proximal portion comprising a first thread configured for fixation with a first cortical layer of a vertebral level, the distal tip extending between a proximal end and a distal end, the distal tip comprising a second thread configured for fixation with a second cortical layer of the vertebral level, the shaft defining only one longitudinal passageway and a socket in communication with the longitudinal passageway, the socket including a first portion having a hexalobular cross section and a second portion, the second portion being continuously tapered from the first portion to the longitudinal cavity, the longitudinal passageway having a distal most end, the distal most end being spaced apart from the distal end of the tip, the shaft further including a first column of fenestrations and a second column of fenestrations, the first column of fenestrations being offset from the second column of fenestrations about the longitudinal axis, the fenestrations each being in communication with the longitudinal passageway, the first and second columns each extending parallel to the longitudinal axis, the first column of fenestrations being spaced radially about the longitudinal axis less than 180 degrees from the second column of fenestrations, the first column of fenestrations including a first fenestration and a second fenestration, the second column of fenestrations including a third fenestration and a fourth fenestration, the third fenestration being positioned along the longitudinal axis between the first fenestration and the second fenestration, the fenestrations being spaced apart from the threads, the shaft being made entirely from one or more of the group consisting of metals, synthetic polymers and ceramics;
a crown positioned in the chamber such that a top surface of the crown defines a portion of the implant cavity and an opposite bottom surface of the crown directly engages a head of the shaft; and a band positioned in the groove such that the head directly engages the band and the band surrounds at least a portion of the shaft to couple the shaft to the receiver.

22. A bone fastener as recited in claim 21, wherein the first thread has a smaller pitch than the second thread.

* * * * *